(12) United States Patent
Heinelt et al.

(10) Patent No.: US 7,442,717 B2
(45) Date of Patent: Oct. 28, 2008

(54) SUBSTITUTED 2-AMINOIMIDAZOLES, PROCESS FOR THEIR PREPARATION, THEIR USE AS MEDICAMENT OR DIAGNOSTIC AID

(75) Inventors: Uwe Heinelt, Wiesbaden (DE); Hans-Jochen Lang, Hofheim (DE); Armin Hofmeister, Oppenheim (DE); Klaus Wirth, Kriftel (DE); Hans-Willi Jansen, Neidernhausen (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 732 days.

(21) Appl. No.: 10/771,185

(22) Filed: Feb. 3, 2004

(65) Prior Publication Data
US 2004/0259927 A1 Dec. 23, 2004

Related U.S. Application Data

(60) Provisional application No. 60/477,570, filed on Jun. 11, 2003.

(30) Foreign Application Priority Data
Feb. 4, 2003 (DE) ................. 103 04 374

(51) Int. Cl.
A61K 31/4168 (2006.01)
C07D 233/88 (2006.01)

(52) U.S. Cl. ............ 514/393; 514/398; 548/302.7; 548/331.5

(58) Field of Classification Search ........ 548/302.7, 548/331.5; 514/393, 398
See application file for complete search history.

(56) References Cited

U.S. PATENT DOCUMENTS

| 3,459,763 | A | * | 8/1969 | Gruenfeld | ............ 548/331.5 |
| 4,275,072 | A | | 6/1981 | Karjalainen et al. | |
| 6,005,010 | A | | 12/1999 | Schwark | |

FOREIGN PATENT DOCUMENTS

| EP | 0254259 | 1/1988 |
| GB | 1131191 | 10/1968 |
| WO | WO90/14338 | 11/1990 |
| WO | WO95/19968 | 7/1995 |
| WO | WO01/21160 | 3/2001 |
| WO | WO01/21582 | 3/2001 |
| WO | WO01/72742 | 10/2001 |
| WO | WO01/79186 | 10/2001 |
| WO | WO02/20496 | 3/2002 |

OTHER PUBLICATIONS

U.S. Appl. No. 09/975,566, filed Oct. 11, 2001, Collins et al.
U.S. Appl. No. 10/448,851, filed May 30, 2003, Lang.
U.S. Appl. No. 10/000,028, filed Dec. 4, 2001, Hofmeister.
U.S. Appl. No. 10/323,799, filed Dec. 20, 2002, Heinelt.
U.S. Appl. No. 09/734,008, filed Dec. 12, 2000, Heinelt.
Akhter, et al., Squalamine, a Novel Cationic Steroid, Specifically Inhibits the Brush-border Na+/H+ Exchanger Isoform NHE3, The American Physiological Society, 1999, pp. c136-c144.
Ernsberger, et al., Clonidine Binds To Imidazole Binding Sites As Well As Alpha2-Adrenoceptors In The Ventrolateral Medulla, European Journal of Pharmacology, 134 (1987) pp. 1-13.
Fliegel, et al., Regulation And Characterization Of The Na+/H+ Exchanger, Biochem. Cell. Biol., 76: (1998), pp. 735-741.
Jen, et al., Amidines and Related Compounds. 6. Studies on Structure-Activity Relationships of Antihypertensive and Antisecretory Agents Related to Clonidine, Journal of Medicinal Chemistry, 1975, vol. 18, No. 1., pp. 90-99.
Ma, et al., Expression And Localization Of Na+/H+ Exchangers In Rat Central Nervous System, Neuroscience. (1997), vol. 79. No. 2. pp. 591-603.
Orlowski, et al., Molecular Cloning Of Putative Members Of The Na/H Exchanger, J. Biological Chemistry, 1992, vol. 267, pp. 9331-9339.

* cited by examiner

*Primary Examiner*—Kamal Saeed
*Assistant Examiner*—Janet L Coppins
(74) *Attorney, Agent, or Firm*—Craig M. Bell

(57) ABSTRACT

Novel substituted 2-aminoimidazoles of formula I, process for their preparation, their use as medicament or diagnostic aid, and medicament containing them. The compounds of this type are useful in the prevention or treatment of various disorders and can be employed inter alia for renal disorders such as acute or chronic renal failure, for disorders of biliary function, for respiratory disorders such as snoring or sleep apneas or for stroke

I

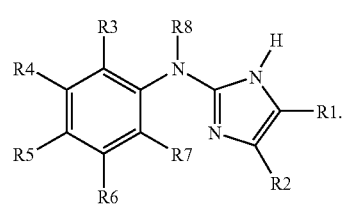

11 Claims, No Drawings

SUBSTITUTED 2-AMINOIMIDAZOLES, PROCESS FOR THEIR PREPARATION, THEIR USE AS MEDICAMENT OR DIAGNOSTIC AID

CROSS REFERENCE TO RELATED APPLICATIONS

This application claims the benefit of German patent application No. 10304374.8, filed Feb. 4, 2003 and the benefit of U.S. Provisional patent application No. 60/477,570, filed Jun. 11, 2003.

FIELD OF THE INVENTION

The invention relates to compounds of 2-aminoimidazoles, which inhibit the sodium proton exchanger, in particular subtype 3 (NHE3), and which can be used in the prevention or treatment of various disorders. Thus, the compounds can be employed inter alia for renal disorders such as acute or chronic renal failure, for disorders of biliary function, for respiratory disorders, for snoring or sleep apneas or for stroke.

SUMMARY OF THE INVENTION

The invention relates to compounds of the formula I

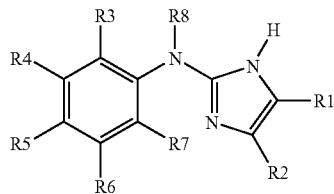

in which the meanings are:

R1 and R2
  together with the two carbon atoms to which they are bonded a five-, six-, seven- or eight-membered carbon ring comprising one or two double bonds,
  where the ring is unsubstituted or substituted by 1, 2, 3, 4, 5, 6, 7, 8, 9, 10, 11 or 12 F atoms and/or with one or two radicals from the group of OH, NR9R10, alkyl with 1, 2, 3 or 4 carbon atoms, CN, $CF_3$ or alkoxy with 1, 2, 3 or 4 carbon atoms R9 and R10 independently of one another H or alkyl with 1, 2, 3 or 4 carbon atoms;

or

R1 and R2
  independently of one another H, alkyl with 1, 2, 3 or 4 carbon atoms CN or phenyl
  where the carbon chains are unsubstituted or substituted independently of one another by 1, 2, 3, 4, 5, 6, 7, 8 or 9 F atoms,
  where R1 and R2 do not both correspond simultaneously to hydrogen;

R3, R4, R5, R6, and R7
  independently of one another H, F, Cl, Br, I, alkyl with 1, 2, 3 or 4 carbon atoms, or alkoxy with 1, 2, 3 or 4 carbon atoms,
  where the carbon chains are unsubstituted or substituted independently of one another by 1, 2, 3, 4, 5, 6, 7, 8 or 9 F atoms,
  where R3 and R7 do not both correspond simultaneously to hydrogen;

R8
  H, alkyl with 1, 2, 3 or 4 carbon atoms or cycloalkyl with 3, 4 or 5 carbon atoms,
  where the carbon chains or cycloalkyl radicals are unsubstituted or substituted by 1, 2, 3, 4, 5, 6, 7, 8 or 9 F atoms;

and the pharmaceutically acceptable salts and trifluoroacetic acid salts thereof;

where R1 and R2 are not both simultaneously methyl when R3 is Cl and R4, R5, R6, R7 and R8 are hydrogen, where (2,6-Dichlorphenyl)-(4-methyl-1H-imidazol-2-yl)-amin is excluded.

Preference is given to compounds of the formula I in which the meanings are

R1 and R2
  together with the two carbon atoms to which they are bonded a five-, six-, seven- or eight-membered carbon ring comprising one or two double bonds,
  where the ring is unsubstituted or substituted by 1, 2, 3, 4, 5, 6, 7, 8, 9, 10, 11 or 12 F atoms and/or by one or two radicals from the group of $CH_3$ or $OCH_3$;

R3, R4, R5, R6 and R7
  independently of one another H, F, Cl, Br, alkyl with 1, 2, 3 or 4 carbon atoms or alkoxy with 1, 2, 3 or 4 carbon atoms,
  where the carbon chains are unsubstituted or substituted independently of one another by 1, 2, 3, 4, 5, 6, 7, 8 or 9 F atoms,
  where R3 and R7 do not both correspond simultaneously to hydrogen;

R8
  H, alkyl with 1, 2, 3 or 4 carbon atoms or cycloalkyl with 3, 4 or 5 carbon atoms,
  where the carbon chains or cycloalkyl radicals are unsubstituted or substituted by 1, 2, 3, 4, 5, 6, 7, 8 or 9 F atoms;

and the pharmaceutically acceptable salts and trifluoroacetic acid salts thereof.

Particular preference is given to compounds of the formula I in which the meanings are:

R1 and R2
  together with the two carbon atoms to which they are bonded a five-, six- or seven-membered carbon ring comprising a double bond, R3 and R7
  independently of one another F, Cl, Br or alkyl with 1, 2, 3 or 4 carbon atoms,
  where the carbon chains are unsubstituted or substituted independently of one another by 1, 2, 3, 4, 5, 6, 7, 8 or 9 F atoms;

R4,R5 and R6
  H

R8
  H or alkyl with 1, 2, 3 or 4 carbon atoms,
  where the carbon chains are unsubstituted or substituted by 1, 2, 3, 4, 5, 6, 7, 8 or 9 F atoms;

and the pharmaceutically acceptable salts and trifluoroacetic acid salts thereof.

Very particular preference is given to:
(2,6-dichlorophenyl)(4,5,6,7-tetrahydro-1H-benzoimidazol-2-yl)amine or (2,6-dichlorophenyl)methyl(4,5,6,7-tetrahydro-1H-benzoimidazol-2-yl)amine and the pharmaceutically acceptable salts and trifluoroacetic acid salts thereof.

Preference is further given to compounds of the formula I in which the meanings are:

R1 and R2
independently of one another H, alkyl with 1, 2, 3 or 4 carbon atoms, CN or phenyl
where the carbon chains are unsubstituted or substituted independently of one another by 1, 2, 3, 4, 5, 6, 7, 8 or 9 F atoms,
where R1 and R2 do not both correspond simultaneously to hydrogen;

R3, R4, R5, R6 and R7
independently of one another H, F, Cl, Br or alkyl with 1, 2, 3 or 4 carbon atoms
where the carbon chains are unsubstituted or substituted independently of one another by 1, 2, 3, 4, 5, 6, 7, 8 or 9 F atoms,
where R3 and R7 do not both correspond simultaneously to hydrogen;

R8
H, alkyl with 1, 2, 3 or 4 carbon atoms or cycloalkyl with 3, 4 or 5 carbon atoms,
where the carbon chains or cycloalkyl radicals are unsubstituted or substituted by 1, 2, 3, 4, 5, 6, 7, 8 or 9 F atoms;

and the pharmaceutically acceptable salts and trifluoroacetic acid salts thereof;

where R1 and R2 are not both simultaneously methyl when R3 is Cl and R4, R5, R6, R7 and R8 are hydrogen, where (2,6-Dichlorphenyl)-(4-methyl-1H-imidazol-2-yl)-amin is excluded.

Particular preference is given to compounds of the formula I in which the meanings are:

R1 and R2
independently of one another H or alkyl with 1, 2, 3 or 4 carbon atoms;

where R1 and R2 do not both correspond simultaneously to hydrogen;

R3 and R7
independently of one another F, Cl, Br or alkyl with 1, 2, 3 or 4 carbon atoms,
where the carbon chains are unsubstituted or substituted independently of one another by 1, 2, 3, 4, 5, 6, 7, 8 or 9 F atoms;

R4, R5 and R6
H

R8
H or alkyl with 1, 2, 3 or 4 carbon atoms,
where the carbon chains are unsubstituted or substituted by 1, 2, 3, 4, 5, 6, 7, 8 or 9 F atoms;

and the pharmaceutically acceptable salts and trifluoroacetic acid salts thereof, where (2,6-Dichlorphenyl)-(4-methyl-1H-imidazol-2-yl)-amin is excluded.

Very particular preference is given to:
(2,6-dichlorophenyl)(4,5-dimethyl-1H-imidazol-2-yl)amine and the pharmaceutically acceptable salts and trifluoroacetic acid salts thereof.

In one embodiment, preferred compounds of the formula I are those in which R1 and R2 form together with the two carbon atoms to which they are bonded a five-, six-, seven or eight-membered carbon ring comprising one or two double bonds, where the ring is unsubstituted or substituted by 1, 2, 3, 4, 5, 6, 7, 8, 9, 10, or 11 F atoms and/or by one or two radicals from the group of $CH_3$ or $OCH_3$; particularly preferred compounds are those in which R1 and R2 form together with the two carbon atoms to which they are bonded a five-, six- or seven-membered, unsubstituted carbon ring comprising one double bond.

In a further embodiment, preferred compounds of the formula I are those in which R1 and R2 are described independently of one another by H or alkyl with 1, 2, 3 or 4 carbon atoms.

In a further embodiment, preferred compounds of the formula I are those in which R3 and R7 are not described by hydrogen; particularly preferred compounds are those in which R3 and R7 are described independently of one another by F, Cl, Br or alkyl with 1, 2, 3 or 4 carbon atoms, where the carbon chains are unsubstituted or substituted independently of one another by 1, 2, 3, 4, 5, 6, 7, 8 or 9 F atoms; very particularly preferred compounds are those in which R3 and R7 are described independently of one another by Cl or methyl, in particular Cl. In a further embodiment, preferred compounds of the formula I are those in which R4, R5 and R6 are described by hydrogen.

In a further embodiment, preferred compounds of the formula I are those in which R8 is described by hydrogen or alkyl with 1, 2, 3 or 4 carbon atoms, and particularly preferred compounds are those in which R8 is described by hydrogen or methyl.

The invention further relates to the use of compounds of the formula I

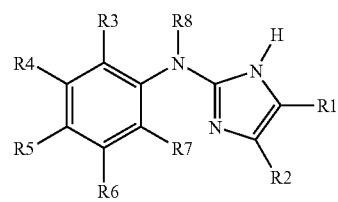

for producing a medicament for the treatment of diseases which can be influenced by inhibition of the sodium/hydrogen exchanger (NHE), in particular of NHE3, in which the meanings are:

R1 and R2
independently of one another H, F, Cl, Br, I, CN, alkyl with 1, 2, 3, 4, 5 or 6 carbon atoms, alkenyl with 2, 3, 4, 5 or 6 carbon atoms, alkynyl with 2, 3, 4, 5 or 6 carbon atoms, cycloalkyl with 3, 4, 5 or 6 carbon atoms, cycloalkenyl with 4, 5 or 6 carbon atoms or phenyl,
where phenyl is unsubstituted or substituted independently of one another by one or two radicals from the group of F, Cl, Br, I, OH, NR9R10, alkyl with 1, 2, 3 or 4 carbon atoms, CN, $CF_3$ or alkoxy with 1, 2, 3 or 4 carbon atoms, with R9, R10 independently of one another H, alkyl with 1, 2, 3 or 4 carbon atoms;
and
where the carbon chains or rings are unsubstituted or substituted independently of one another by 1, 2, 3, 4, 5, 6, 7, 8, 9, 10, 11, 12 or 13 F atoms and/or one or two radicals from the group of OH, NR9R10, alkyl with 1, 2, 3 or 4 carbon atoms, CN, $CF_3$ or alkoxy with 1, 2, 3 or 4 carbon atoms, with R9, R10 independently of one another H, alkyl with 1, 2, 3 or 4 carbon atoms;
where R1 and R2 preferably do not correspond simultaneously to phenyl;

or

R1 and R2
together with the two carbon atoms to which they are bonded a five-, six-, seven- or eight-membered carbon ring comprising one or two double bonds,
where the ring is unsubstituted or substituted by 1, 2, 3, 4, 5, 6, 7, 8, 9, 10, 11 or 12 F atoms and/or one or two radicals from the group of NR9R10, alkyl with 1, 2, 3 or 4 carbon atoms, OH, CN, $CF_3$ or alkoxy with 1, 2, 3 or 4 carbon atoms, with R9, R10 being independently of one another H, alkyl with 1, 2, 3 or 4 carbon atoms;

R3, R4, R5, R6 or R7
independently of one another H, F, Cl, Br, I, alkyl with 1, 2, 3 or 4 carbon atoms, $(C_2-C_4)$-alkenyl, cycloalkyl with 3, 4, 5 or 6 carbon atoms, OH, alkoxy with 1, 2, 3 or 4 carbon atoms, CN, $NO_2$, $NH_2$, alkylamino with 1, 2, 3 or 4 carbon atoms or dialkylamino with, in each case, 1, 2, 3 or 4 carbon atoms,
where the carbon chains or rings are unsubstituted or substituted independently of one another by 1, 2, 3, 4, 5, 6, 7, 8 or 9 F atoms;
where R3 and R7 do not correspond simultaneously to hydrogen;

R8
H, alkyl with 1, 2, 3 or 4 carbon atoms or cycloalkyl with 3, 4 or 5 carbon atoms,
where the carbon chains or rings are unsubstituted or substituted by 1, 2, 3, 4, 5, 6, 7, 8 or 9 F atoms;

and the pharmaceutically acceptable salts thereof.

It is preferred in one embodiment to use compounds of the formula I in which R1 and R2 form together with the two carbon atoms to which they are bonded a five-, six-, seven- or eight-membered carbon ring comprising one or two double bonds, where the ring is unsubstituted or substituted by 1, 2, 3, 4, 5, 6, 7, 8, 9, 10 or 11 F atoms and/or by one or two radicals from the group of $CH_3$ or $OCH_3$; it is particularly preferred to use compounds in which R1 and R2 form together with the two carbon atoms they are bonded a five-, six- or seven-membered, unsubstituted carbon ring comprising one double bond.

It is preferred in a further embodiment to use compounds of the formula I in which R1 and R2 are described independently of one another by H or alkyl with 1, 2, 3 or 4 carbon atoms.

It is preferred in a further embodiment to use compounds of the formula I in which R3 and R7 are not described by hydrogen; it is particularly preferred to use compounds in which R3 and R7 are described independently of one another by F, Cl, Br or alkyl with 1, 2, 3 or 4 carbon, atoms, where the carbon chains are unsubstituted or substituted independently of one another by 1, 2, 3, 4, 5, 6, 7, 8 or 9 F atoms; it is very particularly preferred to use compounds in which R3 and R7 are described independently of one another by Cl or methyl, in particular Cl. It is preferred in a further embodiment to use compounds of the formula I in which R4, R5 and R6 are described by hydrogen. It is preferred in a further embodiment to use compounds of the formula I in which R8 is described by hydrogen or alkyl with 1, 2, 3 or 4 carbon atoms; it is particularly preferred to use compounds in which R8 is described by hydrogen or methyl.

If the substituents R1, R2, R3, R4, R5, R6, R7 or R8 contain one or more centers of asymmetry, these may have, independently of one another, both the S and the R configuration. The compounds may be in the form of optical isomers, of diastereomers, of racemates or of mixtures thereof on all ratios.

The present invention encompasses all tautomeric forms of the compounds of the formula I.

DETAILED DESCRIPTION OF THE INVENTION

Definition:

Carbon chains are all radicals which comprise carbon atoms in straight-chain or branched arrangement, for example 1, 2, 3, 4, 5 or 6 carbon atoms. Examples are alkyl radicals, alkoxy radicals, alkynyl radicals, alkynyl radicals, alkylamino radicals or dialkylamino radicals. Carbon rings are all radicals which comprise carbon atoms which form a ring, for example of 3, 4, 5 or 6 carbon atoms. Examples of carbon rings are cycloalkyl radicals or cycloalkenyl radicals. Carbon chains or rings may be unsaturated and also polyunsaturated in various positions, and one or more, for example 1, 2, 3, 4, 5, 6, 7, 8, 9, 10, 11, 12 or 13, hydrogen atoms in carbon chains or rings may be replaced by fluorine atoms. Substituted carbon chains may be substituted in any positions.

Alkyl radicals may be straight-chain or branched. This applies also when they have substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1, 1-dimethylethyl), n-pentyl, isopentyl, tert-pentyl, neopentyl, n-hexyl, 3-methylpentyl, isohexyl, neohexyl. Preferred alkyl radicals are methyl, ethyl, isopropyl. One or more, for example 1, 2, 3, 4, 5, 6, 7, 8, 9, 10, 11, 12 or 13, hydrogen atoms in alkyl radicals may be replaced by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any positions.

Alkenyl radicals may be straight-chain or branched. This applies also when they have substituents, for example in fluoroalkenyl radicals. The alkenyl radicals may be unsaturated in various positions and also polyunsaturated. Examples of alkenyl radicals are ethenyl, n-prop-1-enyl, n-prop-2-enyl, isoprop-1-enyl (=1-methylethenyl), n-but-1-enyl, n-but-2-enyl, n-but-3-enyl, n-buta-1,3-dienyl, isobut-1-enyl (=2-methylprop-1-enyl), isobut-2-enyl (=2-methylprop-2-enyl), sec-but-1-enyl (=1-methylprop-1-enyl) pentenyl, hexenyl. Preferred alkenyl radicals are ethenyl, n-prop-1-enyl, n-prop-2-enyl, n-but-1-enyl, n-but-2-enyl, n-pentenyl, n-pentadienyl, isopentenyl, tert-pentenyl, neopentenyl, n-hexenyl, n-hexadienyl, n-hexatrienyl, 3-methylpentenyl, isohexenyl, neohexenyl. One or more, for example 1, 2, 3, 4, 5, 6, 7, 8, 9, 10 or 11, hydrogen atoms in alkenyl radicals may be replaced by fluorine atoms. Substituted alkenyl radicals may be substituted in any positions.

Alkynyl radicals may be straight-chain or branched. This applies also when they have substituents, for example in fluoroalkynyl radicals. The alkynyl radicals may be unsaturated in various positions and also polyunsaturated. Examples of alkynyl radicals are ethynyl, n-prop-1-ynyl, n-prop-2-ynyl, n-but-1-ynyl, n-but-2-ynyl, n-but-3-ynyl, n-buta-1,3-diynyl, sec-but-2-ynyl (=1-methylprop-2-ynyl), n-pentynyl, n-pentadiynyl, isopentynyl, tert-pentynyl, neopentynyl, n-hexynyl, n-hexadiynyl, n-hexatriynyl, 3-methylpentynyl, isohexynyl, neohexynyl. Preferred alkynyl radicals are n-prop-1-ynyl, n-prop-2-ynyl, n-but-1-ynyl, n-but-2-ynyl. One or more, for example 1, 2, 3, 4, 5, 6, 7, 8 or 9, hydrogen atoms in alkynyl radicals may be replaced by fluorine atoms. Substituted alkynyl radicals may be substituted in any positions.

Examples of cycloalkyl radicals are cyclpropyl, cyclobutyl, cyclopentyl or cyclohexyl. One or more, for example 1, 2, 3, 4, 5, 6, 7, 8, 9, 10 or 11 hydrogen atoms in cycloalkyl radicals may be replaced by fluorine atoms. Substituted cycloalkyl radicals may be substituted in any positions.

The cycloalkenyl radicals may be unsaturated in various positions and also polyunsaturated. Examples of cycloalkenyl radicals are cyclobut-1-enyl, cyclobut-2-enyl, cyclopentenyl, cyclopentadienyl, cyclohexenyl or cyclohexadienyl. One or more, for example 1, 2, 3, 4, 5, 6, 7, 8 or 9, hydrogen atoms in cycloalkenyl radicals may be replaced by fluorine atoms. Substituted cycloalkenyl radicals may be substituted in any positions.

Phenyl radicals may be unsubstituted or mono- or polysubstituted, for example mono-, di- or trisubstituted, by identical or different radicals. In monosubstituted phenyl radicals, the substituent may be in position 2, position 3 or position 4. Disubstituted phenyl may be substituted in position 2.3, position 2.4, position 2.5, position 2.6, position 3.4 or position 3.5.

A method for preparing the compounds used is also described. Thus, compounds described by formula I can be prepared under acidic conditions in a manner known to the skilled worker from the underlying guanidines of the formula II or a tautomeric form of the formula II

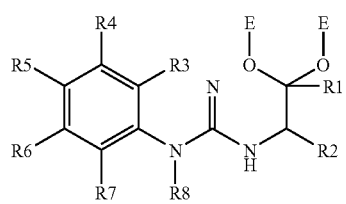

where the radicals R1 to R8 are defined in accordance with formula I, while E corresponds to an alkyl radical having 1 to 4 carbon:atoms, it being possible for the two E radicals also to be connected to form a ring.

Compounds of the formula II can be obtained in a manner known from the literature from the cyanamides of the formula III or compounds of the formula IV and the appropriate amino ketals or acetals of the formula V, where the radical R in formula IV corresponds to an alkyl group, preferably methyl.

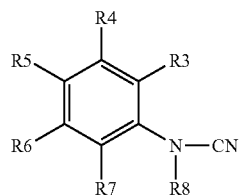

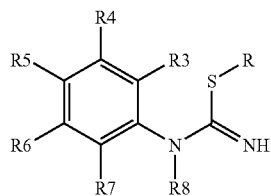

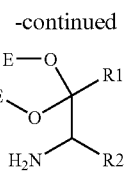

Access to the above intermediates of the formulae III, IV and V for R8 =hydrogen is disclosed in the literature (J. Med. Chem. 1975, 18, 90-99; GB 1, 131, 191).

It has been found that compounds of the formula V can advantageously be prepared, in a modification of the above literature, starting from α-halo ketones or aldehydes via the sequence of halogen-azide exchange (preferably with sodium azide), ketalization or acetalization (preferably with ethylene glycol) and reduction (preferably with hydrogen in the presence of palladium on carbon or platinum dioxide) (scheme 1):

Scheme 1:

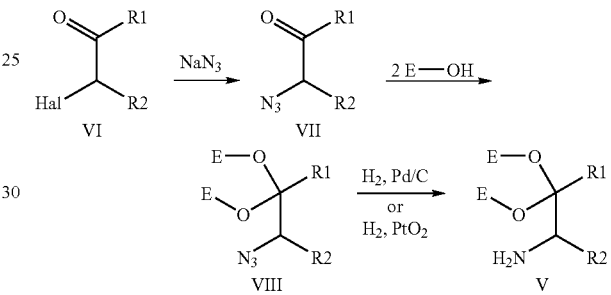

The present invention thus further relates to a process for preparing α-amino ketals of the formula (V)

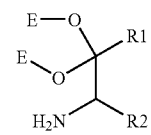

in which the meanings are:

R1 and R2
H, alkyl with 1, 2, 3, 4, 5 or 6 carbon atoms, alkenyl with 2, 3, 4, 5 or 6 carbon atoms, alkynyl with 2, 3, 4, 5 or 6 carbon atoms, cycloalkyl with 3, 4, 5 or 6 carbon atoms, cycloalkenyl with 4, 5 or 6 carbon atoms or phenyl,
where phenyl is unsubstituted or substituted independently of one another by one or two radicals from the group of F, Cl, Br, I, NR11R12, alkyl with 1, 2, 3 or 4 carbon atoms, CN, CF$_3$ or alkoxy with 1, 2, 3 or 4 carbon atoms, with R11, R12 being independently of one another alkyl with 1, 2, 3 or 4 carbon atoms, benzyl, 4-methoxybenzyl; and
where the carbon chains are unsubstituted or substituted independently of one another by 1, 2, 3, 4, 5, 6, 7, 8 or 9 F atoms and/or by one or two radicals from the group of NR11R12, alkyl with 1, 2, 3 or 4 carbon atoms, CN, CF$_3$ or alkoxy with 1, 2, 3 or 4 carbon atoms, with R11, R12 being independently of one another alkyl with 1, 2, 3 or 4 carbon atoms, benzyl, 4-methoxybenzyl;

or

R1 and R2
  together with the two carbon atoms to which they are bonded a five- to eight-membered carbon ring which is saturated or comprises a double bond,
  where the ring is unsubstituted or substituted by 1, 2, 3, 4, 5, 6, 7, 8, 9, 10, 11 or 12 F atoms and/or by one or two radicals from the group of NR11R12, alkyl with 1, 2, 3 or 4 carbon atoms, CN, CF$_3$ or alkoxy with 1, 2, 3 or 4 carbon atoms,
  with
  R11, R12 independently of one another alkyl with 1, 2, 3 or 4 carbon atoms, benzyl, 4-methoxybenzyl;

E
  alkyl with 1, 2, 3 or 4 carbon atoms, or the two E radicals form a cyclic ketal in which E-E is (C$_2$-C$_4$)-alkylene;

Hal
  Cl, Br, I which comprises converting an α-halo ketone or aldehyde of the formula VI with an azide, for example NaN$_3$, by halogen-azide exchange into the corresponding α-azide ketone or aldehyde of the formula VII

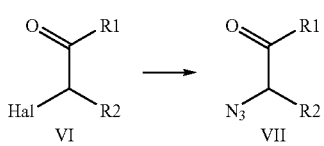

which is subsequently reacted with mono- or dihydric alcohols by ketalization or acetalization to give the α-azide ketal or acetal of the formula VIII

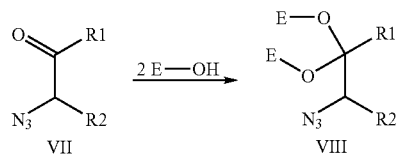

which is then reduced, preferably with hydrogen in the presence of a catalyst for example palladium on carbon or platinum dioxide, to compounds of the formula V.

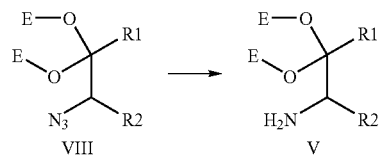

Compounds of the formula I can also be prepared starting from cyanamides of the formula III and α-amino ketones of the formula IX in protic solvents such as alcohols, for example ethanol.

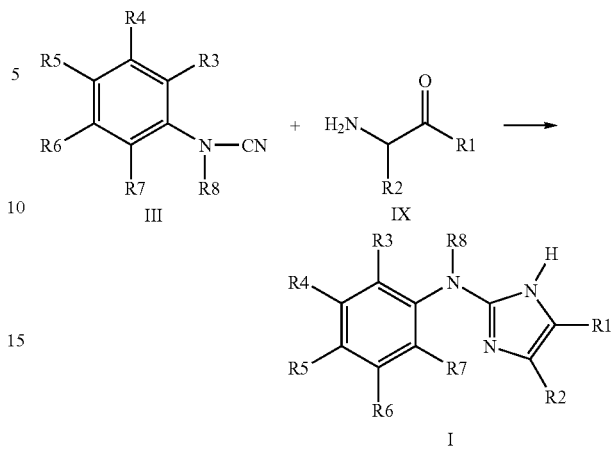

A suitable alternative is also the two-stage reaction of suitable 1,2-diaminoalkylene derivatives of the formula X with isothiocyanates of the formula XI.

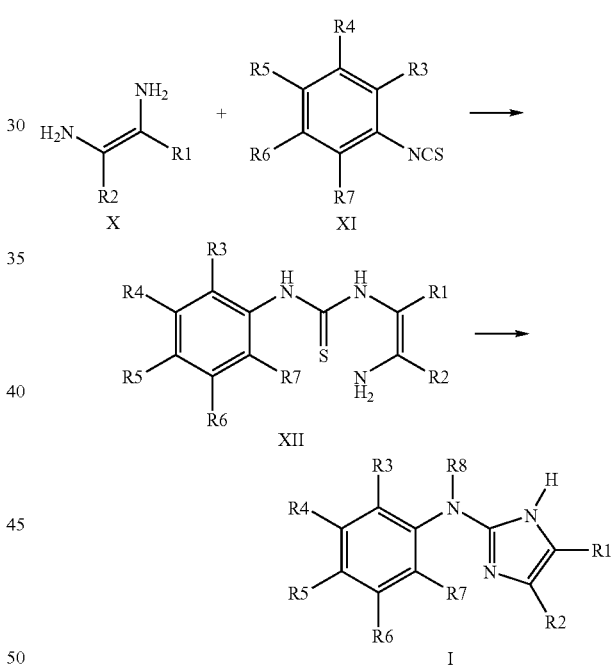

The thiourea of the formula XII which is formed as intermediate is then cyclized preferably with N,N'-dicyclohexyl-carbodiimide or methyl iodide to give compounds of the formula I.

The starting compounds of the formulae IX and X are commercially available or can be prepared by, or in analogy to, processes described in the literature and known to the skilled worker.

It was surprisingly possible to show in the present invention that the described compounds are potent inhibitors of the sodium/hydrogen exchanger (NHE), in particular of NHE3.

NHE3 is found in the body of various species preferentially in the bile, the intestine and the kidney (Fliegel et al, Biochem. Cell. Biol. 76: 735-741, 1998), but has also been detected in the brain (E. Ma et al. Neuroscience 79: 591-603).

Known NHE3 inhibitors are derived, for example, from compounds of the acylguanidine type (EP 825 178), norbornylamine type (DE 199 60 204), 2-guanidinoquinazoline type (WO 01 79 186, WO 02 20496) or benzamidine type (WO 01 21582, WO 01 72 742). Squalamine, which is likewise described as NHE3 inhibitor (M. Donowitz et al. Am. J. Physiol. 276 (Cell Physiol. 45: C136-C144), does not act directly like the compounds of formula I but reaches its maximum strength of effect only after one hour.

NHE3 inhibitors of the imidazolidine type are described in German patent application DE 10163239 and of the thiophene type in German patent application DE 10224892. WO 02 46169 A1 describes NHE3 inhibitors of the 2-phenylaminobenzimidazole type. It has now been found, surprisingly, that the imidazole derivatives of the formula I described herein are likewise potent inhibitors of NHE3 and moreover have advantageous pharmacological properties.

Clonidine, which is similar to the compounds described herein, is known as a weak NHE inhibitor. Its effect on the rat NHE3 is indeed extremely moderate, with an $IC_{50}$ of 620 μM. Instead, it shows a certain selectivity for NHE2, for which it has an $IC_{50}$ of 42 μM (J. Orlowski et al J. Biol. Chem. 268, 25536). It should therefore rather be referred to as an NHE2 inhibitor. Besides the weak NHE effect, clonidine has a high affinity for the adrenergic α2 receptor and imidazoline I1 receptor, mediating a strong blood pressure-lowering effect (Ernsberger et al Eur. J. Pharmacol. 134, 1, 1987). Compounds of the formula I are distinguished by an increased NHE3-inhibiting effect compared with clonidine.

On the basis of these unexpected NHE-inhibitory properties, the compounds of the formula I are suitable for the prevention and treatment of diseases caused by an activation or by an activated NHE. The use of the compounds of the invention relates to the prevention and treatment of acute and chronic diseases in veterinary and human medicine.

Thus, NHE inhibitors of the invention are suitable for the treatment of diseases caused by ischemia and/or by reperfusion.

The compounds described herein are, as a result of their pharmacological properties, outstandingly suitable as antiarrhythmic drugs with a cardioprotective component for prophylaxis of infarction and for treatment of infarction, and for the treatment of angina pectoris, in which connection they also inhibit or greatly reduce in a preventive manner the pathophysiological processes associated with the development of ischemia-induced damage, in particular in the induction of ischemia-induced cardiac arrhythmias. Because of their protective effects against pathological hypoxic and ischemic situations, the compounds of the formula I which are used according to the invention can, as a result of inhibition of the cellular $Na^+/H^+$ exchange mechanism, be used as drugs for the treatment of all acute or chronic damage induced by ischemia or disorders induced primarily or secondarily thereby. This relates to the use thereof as drugs for surgical interventions, e.g. in organ transplantations, in which cases the compounds can be used both to protect the organs in the donor before and during removal, to protect removed organs for example on treatment with or storage thereof in physiological bath fluids, as well as during the transfer into the recipient organism. The compounds are likewise valuable drugs with a protective action during the performance of angioplastic surgical interventions, for example on the heart as well as peripheral vessels.

In accordance with their protective action against ischemia-induced damage, the compounds are also suitable as drugs for the treatment of ischemias of the nervous system, especially of the CNS, in which connection they are suitable for example for the treatment of stroke or of cerebral edema.

In addition, the compounds of the formula I which are used according to the invention are likewise suitable for the treatment of types of shock, such as, for example, of allergic, cardiogenic, hypovolemic and bacterial shock.

In addition, the compounds induce an improvement in the respiratory drive and are therefore used to treat respiratory conditions associated with the following clinical conditions and diseases: disturbance of central respiratory drive (e.g. central sleep apneas, sudden infant death, postoperative hypoxia), muscle-related breathing disorders, breathing disorders after long-term ventilation, breathing disorders associated with altitude adaptation, obstructive and mixed type of sleep apneas, acute and chronic pulmonary disorders with hypoxia and hypercapnia.

The compounds additionally increase the tone of the muscles of the upper airways, so that snoring is suppressed.

A combination of an NHE inhibitor with a carbonic anhydrase inhibitor (e.g. acetazolamide), the latter inducing metabolic acidosis and thus itself increasing respiratory activity, proves to be advantageous due to an enhanced effect and reduced use of active ingredient.

The compounds described herein are additionally suitable as medicaments for the therapy and prophylaxis of disorders and impairment induced by overexcitability of the central nervous system, especially for the treatment of epileptiform disorders, centrally induced klonic and tonic spasms, states of mental depression, anxiety disorders and psychoses. The NHE inhibitors described herein may moreover be used alone or in combination with other substances having antiepileptic activity or antipsychotic active ingredients, or carbonic anhydratase inhibitors, for example with acetazolamide, and with other inhibitors of NHE or of the sodium-dependent chloride-bicarbonate exchanger (NCBE).

It has emerged that the compounds used according to the invention have a mild laxative effect and accordingly can be used advantageously as laxatives or if there is a risk of constipation.

The compounds of the invention can additionally be used advantageously for the prevention and therapy of acute and chronic disorders of the intestinal tract caused by ischemic states in the intestinal region and/or by subsequent reperfusion. Such complications may be induced for example by inadequate bowel peristalsis, like those for example to be observed frequently after surgical interventions, associated with constipation or greatly reduced bowel activity.

There is also the possibility of preventing the formation of gallstones.

The compounds of the formula I used according to the invention are furthermore distinguished by a strong inhibitory effect on the proliferation of cells, for example of fibroblast cell proliferation and the proliferation of smooth vascular muscle cells. The compounds of the formula I are therefore suitable as valuable therapeutic agents for diseases in which cell proliferation represents a primary or secondary cause, and can therefore be used as antiatherosclerotic agents, agents to prevent late complications of diabetes, agents to prevent chronic renal failure, cancers, fibrotic disorders of the heart, and pulmonary fibrosis, hepatic fibrosis or renal fibrosis, organ hypertrophies and hyperplasias, for example of the heart and prostate, and thus be used for the prevention and treatment of (congestive) heart failure or for prostate hyperplasia or prostate hypertrophy.

The compounds according to the invention are effective inhibitors of the cellular sodium-proton antiporter (Na/H exchanger) which is elevated in numerous disorders (essential hypertension, atherosclerosis, diabetes, etc.), also in those cells which are readily amenable to measurements, such as, for example, in erythrocytes, platelets or leukocytes. The compounds used according to the invention are therefore suitable as excellent and simple scientific tools, for example in their use as diagnostic aids for determining and distinguishing different types of hypertension, but also of atherosclerosis, of diabetes and late complications of diabetes, proliferative disorders etc.

The compounds of the formula I are moreover suitable for preventive therapy to prevent the development and for the treatment of high blood pressure, for example of essential hypertension, because they reduce or completely inhibit the reabsorption of NaCl in the tubular system of the kidneys. Accordingly, they are also outstandingly suitable as combination and formulation partners for drugs used for treating high blood pressure. Examples of possible combinations are diuretics having a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene. The NHE inhibitors of the present invention can further be used in combination with ACE inhibitors such as, for example, ramipril, enalapril or captopril. Further beneficial combination partners are also β-blockers.

The described NHE inhibitors can likewise be used in the prevention and for the treatment of thrombotic disorders because, as NHE inhibitors, they are able to inhibit both platelet aggregation itself and, in addition, able to inhibit or prevent the excessive release of coagulation mediators, in particular of von Willebrand factor. The NHE inhibitors of the present invention can therefore be combined with further anticoagulant active ingredients such as, for example, acetylsalicylic acid, thrombin antagonists, factor Xa antagonists, drugs with fibrinolytic activity, factor VIIa antagonists etc. Combined use of the present NHE inhibitors with NCBE inhibitors is particularly beneficial.

It has additionally been found that NHE inhibitors show a beneficial effect on serum lipoproteins. It is generally acknowledged that blood lipid levels which are too high, so-called hyperlipoproteinemias, represent a considerable risk factor for the development of arteriosclerotic vascular lesions, especially coronary heart disease. The reduction of elevated serum lipoproteins therefore has exceptional importance for the prophylaxis and regression of atherosclerotic lesions. The compounds used according to the invention can therefore be used for the prophylaxis and regression of atherosclerotic lesions by eliminating a causal risk factor. The NHE inhibitors of the invention can also be combined in a beneficial manner with other antiarteriosclerotic active ingredients such as a substance from the class of fibrates, an upregulator of LD2 receptor activity such as MD-700 and LY295427 or a cholesterol or bile acid absorption inhibitor or an antihypercholesterolemic agent from the class of statins, such as, for example, pravastatin, lovastatin, simvastatin.

With this protection of the vessels against the syndrome of endothelial dysfunction, compounds of the formula I are valuable drugs for the prevention and treatment of coronary vasospasms, peripheral vascular diseases such as intermittent claudication, of atherogenesis and of atherosclerosis, of left-ventricular hypertrophy and of dilated cardiomyopathy, and thrombotic disorders.

Said compounds can likewise be used for the treatment of diseases caused by protozoa and are particularly suitable as antimalarials.

The compounds are additionally suitable for controlling sucking parasites such as mosquitoes, ticks, fleas and plant pests.

In accordance with their protective effects, the compounds are also suitable as drugs for maintaining health and prolonging life.

The NHE inhibitors described herein can generally be combined in a beneficial manner with other compounds regulating the intracellular pH, suitable combination partners being inhibitors of the carbonic anhydratase enzyme group, inhibitors of the bicarbonate ion-transporting systems such as the sodium-bicarbonate cotransporter or the sodium-dependent chloride-bicarbonate exchanger, and other NHE inhibitors, for example having an inhibitory effect on other NHE subtypes, because the pharmacologically relevant pH-regulating effects of the NHE inhibitors described herein can be enhanced thereby.

Said compounds are therefore advantageously used for producing a medicament for the prevention and treatment of sleep apneas and muscle-related respiratory disorders; for producing a medicament for the prevention and treatment of snoring; for producing a medicament for lowering blood pressure; for producing a medicament with a laxative effect for the prevention and treatment of intestinal blockages; for producing a medicament for the prevention and treatment of disorders induced by ischemia and reperfusion of central and peripheral organs, such as acute renal failure, stroke, endogenous states of shock, intestinal disorders etc.; for producing a medicament for the treatment of late damage from diabetes and chronic renal disorders, in particular of all inflammations of the kidneys (nephritides) which are associated with increased protein/albumin excretion; for producing a medicament for the treatment of hypercholesterolemia; for producing a medicament for the prevention of atherogenesis and of atherosclerosis; for producing a medicament for the prevention and treatment of diseases induced by elevated cholesterol levels; for producing a medicament for the prevention and treatment of diseases induced by endothelial dysfunction; for producing a medicament for the treatment of infestation by ectoparasites; for producing a medicament for the treatment of said disorders in combinations with hypotensive substances, preferably with angiotensin converting enzyme (ACE) inhibitors, with diuretics, aldosterone antagonists and angiotensin receptor antagonists. A combination of an NHE inhibitor of the formula I with an active ingredient lowering the blood lipid level, preferably with an HMG-CoA reductase inhibitor (e.g. lovastatin or pravastatin), the latter bringing about a hypolipidemic effect and thus increasing the hypolipidemic properties of the NHE inhibitor of the formula I, proves to be a beneficial combination with enhanced effect and reduced use of active ingredient.

The administration of sodium-proton exchange inhibitors of the formula I as novel drugs for lowering elevated blood lipid levels, and the combination of sodium-proton exchange inhibitors with hypotensive drugs and/or drugs with hypolipidemic activity is claimed.

The invention also relates to a curative composition for human, veterinary or phytoprotective use comprising an effective amount of a compound of the formula I and/or of a pharmaceutically acceptable salt thereof, as well as curative compositions for human, veterinary or phytoprotective use comprising-an effective amount of a compound of the formula I and/or of a pharmaceutically acceptable salt thereof alone or in combination with one or more other pharmacological active ingredients or drugs.

Drugs which comprise a compound of the formula I can in this connection be administered orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine, and in crop protection.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3,% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I for a patient weighing about 75 kg is at least 0.001 mg/kg, preferably 0.1 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 200 mg/kg a day may be necessary, in particular on i.v. administration, for example for a patient with infarction in the intensive care unit.

Pharmaceutically acceptable salts are prepared for example via the following acids: from inorganic acids such as hydrochloric acid, sulfuric acid or phosphoric acid or from organic acids such as acetic acid, citric acid, tartaric acid, lactic acid, malonic acid, methanesulfonic acid, fumaric acid. Suitable acid addition salts in this connection are salts of all pharmacologically acceptable acids, for example halides, especially hydrochlorides, lactates, sulfates, citrates, tartrates, acetates, phosphates, methylsulfonates, p-toluenesulfonates, adipates, fumarates, gluconates, glutamates, glycerolphosphates, maleates and pamoates (this group also corresponds to the physiologically acceptable anions); but also trifluoroacetates.

DESCRIPTIONS OF EXPERIMENTS AND EXAMPLES

List of Abbreviations Used:

| | |
|---|---|
| $R_t$ | retention time |
| TFA | trifluoroacetic acid |
| LCMS | liquid chromatography mass spectroscopy |
| MS | mass spectroscopy |
| CI | chemical ionization |
| ES | electrospray |

General:

Retention times ($R_t$) stated below refer to LCMS measurements with the following parameters:

Method A:

| | |
|---|---|
| stationary phase: | Merck Purospher, 3μ, 2 × 55 mm |
| mobile phase: | 95% $H_2O$ (0.05% TFA) → 95% acetonitrile, 4 min; 95% acetonitrile, 1.5 min; → 5% acetonitrile, 1 min; 0.5 ml/min. |

Method B:

| | |
|---|---|
| stationary phase: | YMC J'sphere ODS H80, 2 × 33 mm |
| Mobile phase: | 95% $H_2O$ (0.05% TFA) → 95% acetonitrile, 2.3 min; 95% acetonitrile, 1 min; → 5% acetonitrile, 0.1 min; 1 ml/min. |

Method C:

| | |
|---|---|
| stationary phase: | YMC J'sphere ODS H80, 2 × 33 mm |
| Mobile phase: | 90% $H_2O$ (0.05% TFA) → 95% acetonitrile, 2.5 min; 95% acetonitrile, 0.8 min; → 10% acetonitrile, 0.05 min; 1 ml/min. |

Method D:

| | |
|---|---|
| stationary phase: | Merck Purospher, 3μ, 2 × 55 mm |
| mobile phase: | 95% $H_2O$ (0.1% HCOOH) → 95% acetonitrile (0.1% HCOOH), 5 min; → 95% acetonitrile (0.1% HCOOH), 2 min; → 95% $H_2O$ (0.1% HCOOH), 1 min; 0.45 ml/min. |

Method E:

| | |
|---|---|
| stationary phase: | YMC J'sphere ODS H80, 2 × 33 mm |
| mobile phase: | 98% $H_2O$ (0.05% TFA) + 2% acetonitrile, 0.3 min; 98% $H_2O$ (0.05% TFA) → 95% acetonitrile, 2 min; 95% acetonitrile, 0.4 min; 1 ml/min. |

The preparative HPLC was carried out under the following conditions:

| | |
|---|---|
| stationary phase: | Merck Purospher RP18 (10 μM) 250 × 25 mm |
| mobile phase: | 90% $H_2O$ (0.05% TFA) → 90% acetonitrile, 40 min; 25 ml/min. |

Example 1

(2,6-Dichlorophenyl)(1H-imidazol-2-yl)amine hydrochloride

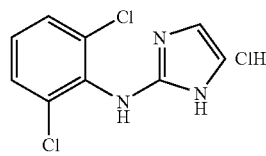

(2,6-Dichlorophenyl)(1H-imidazol-2-yl)amine hydrochloride was prepared by a method disclosed in the literature (J. Med. Chem., 1975, 18, 90-99; GB 1131191).
MS-Cl+: 228.1; LCMS-$R_t$ (A)=2.92 min Example 2

(2,6-Dichlorophenyl)(4-methyl-1H-imidazol-2-yl) amine hydrochloride

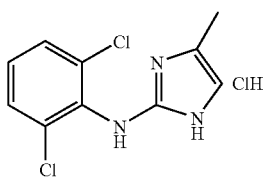

a) 2-(2-Oxopropyl)isoindole-1,3-dione

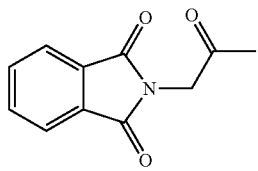

Phthalimide (3 g) was dissolved in dry tetrahydrofuran (70 ml) and added dropwise at room temperature to a suspension of sodium hydride (539 mg) in tetrahydrofuran (15 ml). This was followed by heating at 40° C. for one hour, and then a solution of chloroacetone (1.99 g) dissolved in tetrahydrofuran (15 ml) was added dropwise. The mixture was then kept at the reflux temperature for 15 hours. After cooling, it was added to an ice/water mixture and extracted three times with ethyl acetate. The combined organic phases were washed once with saturated sodium chloride solution and then dried over magnesium sulfate. The solvent was removed in vacuo and the residue was chromatographed on silica gel (n-heptane/ethyl acetate 2:1). 2.9 g of the title compound were isolated.
MS-Cl+: 204.2; LCMS-$R_t$ (C)=1.60 min b) C-(2-Methyl-[1,3]dioxolan-2-yl)methylamine

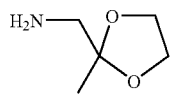

2-(2-Oxopropyl)isoindole-1,3-dione (2.9 g) was mixed in toluene (60 ml) with ethylene glycol (1.71 ml) and para-toluenesulfonic acid (271 mg) and heated with a water trap for 15 hours. The mixture was subsequently dried in vacuo and the residue was dissolved in ethanol (120 ml). Addition of hydrazine (1 g) was followed by heating at 65° C. for one hour and then addition of a further gram of hydrazine. The heating was stopped after a further 1.5 hours at 65° C. After standing overnight, the precipitate which had formed was filtered off with suction and the filtrate was concentrated in vacuo. The residue was suspended in ethanol and again filtered. Concentration of the filtrate resulted in 1.9 g of the amine which could be employed directly in the next stage.
MS-Cl+: 118.2; LCMS-$R_t$ (B)=0.16 min c) N-(2,6-Dichlorophenyl)-N'-(2-methyl-[1,3]dioxolan-2-ylmethyl)guanidine trifluoroacetic acid salt

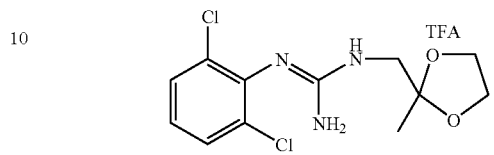

2,6-Dichlorophenylcyanamide (100 mg, prepared as described in J. Med. Chem., 1975, 18, 90-99) and C-(2-methyl-[1,3]dioxolan-2-yl)methylamine (69 mg) were mixed in a flask and heated at 150° C. for 0.5 hours. Water and dichloromethane were added to the cooled reaction mixture. Separation of the phases was followed by extraction twice with dichloromethane. The combined organic phases were dried over magnesium sulfate, filtered and concentrated. The residue was purified by preparative HPLC. The product-containing fractions were combined, the acetonitrile was stripped off in a rotary evaporator and freeze dried. 29 mg of the desired guanidine were obtained.
MS-Cl+: 304.2; LCMS-$R_t$ (B)=1.51 min d) (2,6-Dichlorophenyl)(4-methyl-1H-imidazol-2-yl)amine hydrochloride N-(2,6-Dichlorophenyl)-N'-(2-methyl-[1,3]dioxolan-2-ylmethyl)guanidine trifluoroacetic acid salt (29 mg) was mixed with 1 ml of concentrated hydrochloric acid and heated at 90° C. for 30 min. Cooling was followed by dilution with water and addition of dichloromethane. The mixture was then made alkaline with saturated sodium bicarbonate solution and extracted twice with dichloromethane. The combined organic phases were dried over magnesium sulfate, filtered and concentrated. The residue was mixed with hydrochloric acid and freeze dried. 14 mg of the title compound were obtained.
MS-Cl+: 242.2; LCMS-$R_t$ (B)=1.42 min Example 3

(2,6-Dichlorophenyl)(4,5-dimethyl-1H-imidazol-2-yl)amine hydrochloride

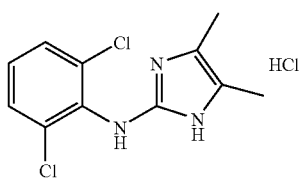

The title compound was prepared in analogy to Example 2 starting from 3-bromo-2-butanone.
MS-Cl+: 256.2; LCMS-$R_t$ (C)=1.43 min

Example 4

(2,6-Dichlorophenyl)(4-methyl-5-phenyl-1H-imidazol-2-yl)amine hydrochloride

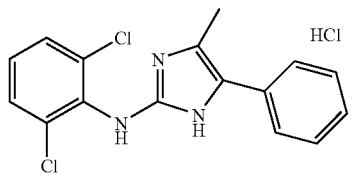

1-Amino-1-phenylacetone hydrochloride (189 mg), 2,6-dichlorophenylcyanamide (187 mg, prepared as described in J. Med. Chem., 1975, 18, 90-99) and triethylamine (101 mg) were kept at the reflux temperature in ethanol (10 ml) for 3 hours. Cooling was followed by drying in vacuo and purification by preparative HPLC. The product-containing fractions were combined, the acetonitrile was stripped in a rotary evaporator, and the aqueous residue was neutralized with potassium carbonate and extracted three times with ethyl acetate. Drying over magnesium sulfate was followed by evaporation to dryness and, after addition of hydrochloric acid, freeze drying. 26 mg of the title compound were obtained.

MS-Cl+: 318.2; LCMS-$R_t$ (A)=4.14 min

Example 5

(2,6-Dichlorophenyl)(4,5,6,7-tetrahydro-1H-benzoimidazol-2-yl)amine hydrochloride

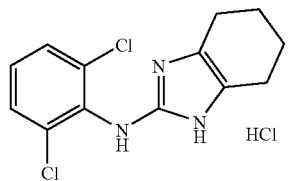

a) 1,4-Dioxaspiro[4.5]dec-6-ylamine

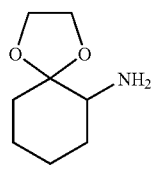

2-Chlorocyclohexanone (5 g) was dissolved in DMSO (10 ml), and sodium azide (7.06 g) dissolved in DMSO (150 ml) was slowly added dropwise at room temperature. The mixture was then stirred at room temperature for 60 minutes. Ice-water was added to the reaction mixture, which was then extracted three times with n-pentane (100 ml). The combined organic phases were washed once with water and dried over magnesium sulfate, and the solvent was concentrated not quite to dryness. This was followed by coevaporation with toluene to remove remaining pentane. The residue was diluted with abs. toluene (120 ml), mixed with ethylene glycol (4.8 g) and a catalytic amount of p-toluenesulfonic acid and heated with a water trap for 5 hours. Standing overnight was followed by heating with a water trap for a further 6 hours. In addition, a further spatula tip of p-toluenesulfonic acid and ethylene glycol (6 ml) were added. The reaction mixture was then washed with water, and the organic phase was extracted once more with toluene. The combined organic phases were dried over magnesium sulfate, and solvent was very substantially removed. The residue was taken up in methanol (40 ml), transferred into a shaking apparatus and, after addition of platinum dioxide (15 mg) and introduction of hydrogen, hydrogenated for 2 hours. The platinum dioxide was filtered off and the solvent was concentrated. The crude product was chromatographed on a silica gel column (mobile phase dichloromethane/methanol/conc. ammonia: 10:0.5:0.1). 1.105 g of an oily product were obtained.

MS-ES+: 158.2; LCMS-$R_t$ (E)=0.38 min b) N-(2,6-Dichlorophenyl)-N'-(1,4-dioxaspiro[4.5]dec-6-yl)guanidine

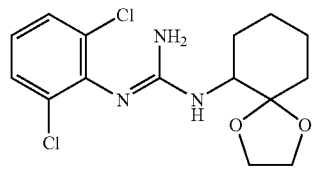

1,4-Dioxaspiro[4.5]dec-6-ylamine (500 mg) was reacted with 2,6-dichloro-phenylcyanamide (595 mg, prepared as described in J. Med. Chem., 1975, 18, 90-99) at 130° C. After 45 minutes, the reaction was stopped and the reaction product was purified by preparative HPLC. The product-containing fractions were combined, the acetonitrile was stripped off in a rotary evaporator, and the aqueous residue was neutralized with potassium carbonate and extracted three times with dichloromethane. Drying over magnesium sulfate was followed by evaporation to dryness. 476 mg of the desired guanidine were obtained.

MS-ES+: 344.2; LCMS-$R_t$ (D)=2.10 min c) (2,6-Dichlorophenyl)(4,5,6,7-tetrahydro-1H-benzoimidazol-2-yl)amine hydrochloride N-(2,6-Dichlorophenyl)-N'-(1,4-dioxaspiro[4.5]dec-6-yl)guanidine (426 mg) was mixed with concentrated HCl (5 ml) and stirred at room temperature for 5 minutes. The resulting precipitate was filtered off and washed with concentrated hydrochloric acid. On dilution of the filtrate with water, a further precipitate separated out and was likewise filtered off. The combined precipitates afforded 311 mg of the desired compound.

MS-ES+: 282.19; LCMS-$R_t$ (D)=2.01 min

Example 6

2-(2,6-Dichlorophenylamino)-1H-imidazole-4,5-dicarbonitrile

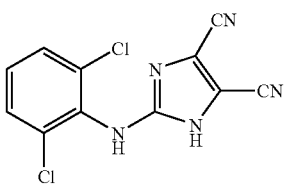

Diaminomaleonitrile (500 mg) was dissolved in absolute tetrahydrofuran (7.5 ml), and 2,6-dichlorophenyl isothiocyanate was added. After stirring at room temperature for 3 hours and leaving to stand overnight, the solvent was stripped off and the residue was purified. The product-containing fractions were combined, acetonitrile was stripped off in a rotary evaporator, and the aqueous residue was neutralized with potassium carbonate and extracted three times with ethyl acetate. Drying over magnesium sulfate was followed by evaporation to dryness. 73 mg of the desired thiourea intermediate were obtained. This product was stirred with N,N'-dicyclohexylcarbodiimide (48 mg) in absolute tetrahydrofuran at room temperature for 5 days. The solvent was stripped off and the residue was purified by preparative HPLC. The product-containing fractions were combined, the acetonitrile was stripped off in a rotary evaporator, and the aqueous residue was neutralized with potassium carbonate and extracted three times with ethyl acetate. Drying over magnesium sulfate was followed by evaporation to dryness, and the residue was freeze dried. 16 mg of the desired imidazole were obtained.

MS-Cl+: 278.2; LCMS-$R_t$ (B)=2.14 min

Example 7

(2,6-Dichlorophenyl)methyl (4,5,6,7-tetrahydro-1H-benzoimidazol-2-yl)amine hydrochloride

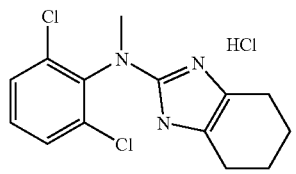

a) (2,6-Dichlorophenyl)methylcyanamide

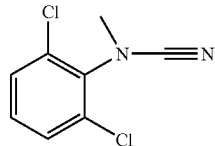

2,6-Dichlorophenylcyanamide (1 g, prepared as described in J. Med. Chem., 1975, 18, 90-99) was dissolved in dry dimethylformamide (25 ml), and powdered potassium carbonate (739 mg) was added. After stirring at room temperature for five minutes, methyl iodide (1.52 g) was added dropwise, and the mixture was stirred at room temperature for two hours. The residue after stripping off the solvent was taken up with water and extracted three times with ether. The combined organic phases were dried over magnesium sulfate and filtered. The residue after stripping of the solvent was purified by preparative HPLC. The product-containing fractions were combined, the acetonitrile was stripped off in a rotary evaporator, and the aqueous residue was neutralized with potassium carbonate and extracted three times with ethyl acetate. Drying over magnesium sulfate was followed by evaporation to dryness. 600 mg of the desired product were obtained.

MS-ES+: 201.1; LCMS-$R_t$ (B)=2.23 min b) N-(2,6-Dichlorophenyl)-N'-(1,4-dioxaspiro[4.5]dec-6-yl)-N-methylguanidine

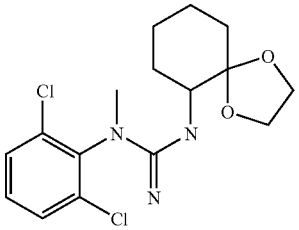

A solution of (2,6-dichlorophenyl)methylcyanamide (25 mg) dissolved in dry tetrahydrofuran (5 ml) was added dropwise to a boiling solution of 1,4-dioxaspiro[4.5]dec-6-ylamine (195 mg, Example 5) in dry THF (5 ml), and the tetrahydrofuran was removed in vacuo. The residue was then heated in an oil bath at 130° C. for 15 minutes and subsequently purified by preparative HPLC. The product-containing fractions were combined, acetonitrile was stripped off in a rotary evaporator, and the aqueous residue was neutralized with potassium carbonate and extracted three times with ethyl acetate. Drying over magnesium sulfate was followed by evaporation to dryness, and the residue was freeze dried. 18 mg of the desired product were obtained.

MS-ES+: 358.4; LCMS-$R_t$ (E)=1.48 min c) (2,6-Dichlorophenyl)methyl(4,5,6,7-tetrahydro-1H-benzoimidazol-2-yl)amine hydrochloride Concentrated HCl (1 ml) was added to N-(2,6-dichlorophenyl)-N'-(1,4-dioxaspiro[4.5]dec-6-yl)-N-methylguanidine (18 mg). After 10 minutes, the mixture was diluted with water and freeze dried. The resulting product was coevaporated with toluene three times.

16 mg of the title compound were obtained.
MS-ES+: 296.17; LCMS-$R_t$ (D)=2.12 min Pharmacological Data:

Description of Test:

In this test, the recovery in the intracellular pH ($pH_i$) after an acidification was ascertained, which is initiated if the NHE3 is capable of functioning, even under bicarbonate-free conditions. For this purpose, the $pH_i$ was determined using the pH-sensitive fluorescent dye BCECF (Calbiochem, the precursor BCECF-AM is employed). The cells (fibroblasts, LAP 1 cells) were initially loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the $pH_i$ using calibration curves. The cells were incubated in $NH_4Cl$ buffer (pH 7.4) ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 is adjusted with 1 M NaOH) even during the BCECF loading. The intracellular acidification was induced by adding 975 µl of an $NH_4Cl$-free buffer (see below) to 25 µl aliquots of the cells incubated in $NH_4Cl$ buffer. The subsequent rate of pH recovery was recorded for three minutes. To calculate the inhibitory potency of the tested substances, the cells were initially investigated in buffers with which a complete or absolutely no pH recovery took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is adjusted with 1 M NaOH). To determine the 0% value, the cells were incubated in an Na⁺-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose, a pH of 7.0 is adjusted with 1 M KOH). The substances to be tested were made up in the Na⁺-containing buffer. The recovery of the intracellular pH at each test concentration of a substance was expressed as a percentage of the maximum recovery. The IC$_{50}$ value for the particular substance for the individual NHE subtypes was calculated from the pH recovery percentages using the Sigma-Plot program.

Results:

| Example | IC$_{50}$ [μM], (rNHE3) |
|---|---|
| Clonidine | 620*) |
| 1 | 7.7 |
| 2 | 1.7 |
| 3 | 0.84 |
| 5 | 0.24 |
| 6 | 98 |
| 7 | 0.28 |

*)Ref.: J. Orlowski et al J. Biol. Chem. 268, 25536

We claim:

1. A compound of formula I, or a pharmaceutically acceptable salt or trifluoroacetic acid salt of said compound:

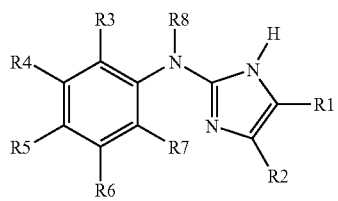

where:
R1 and R2 together with the two carbon atoms to which they are bonded, form a five-, six-, seven- or eight-membered carbon ring comprising one or two double bonds, said ring being substituted by 0, 1, 2, 3, 4, 5, 6, 7, 8, 9, 10, 11 or 12 fluorine atoms and further substituted by 0, 1, or 2 radicals selected from the group consisting of OH, NR9R10, alkyl with 1, 2, 3 or 4 carbon atoms, CN, CF$_3$ and alkoxy with 1, 2, 3 or 4 carbon atoms, wherein R9 and R10 are independently H or alkyl with 1, 2, 3 or 4 carbon atoms; or,
R3, R4, R5, R6 and R7 are independently selected from the group consisting of hydrogen, F, Cl, Br, I, alkyl with 1, 2, 3 or 4 carbon atoms and substituted by 0, 1, 2, 3, 4, 5, 6, 7, 8 or 9 fluorine atoms, and alkoxy with 1, 2, 3 or 4 carbon atoms and substituted by 0, 1, 2, 3, 4, 5, 6, 7, 8 or 9 fluorine atoms, provided that R3 and R7 are not both simultaneously hydrogen;
R8 is selected from the group consisting of H, alkyl with 1, 2, 3 or 4 carbon atoms and substituted by 0, 1, 2, 3, 4, 5, 6, 7, 8 or 9 fluorine atoms, and cycloalkyl with 3, 4 or 5 carbon atoms and substituted by 0, 1, 2, 3, 4, 5, 6, 7, 8 or 9 fluorine atoms.

2. The compound or salt of claim 1, wherein:
R1 and R2, together with the two carbon atoms to which they are bonded, form a five-, six-, seven or eight-membered carbon ring comprising one or two double bonds, said ring being substituted by 0, 1, 2, 3, 4, 5, 6, 7, 8, 9, 10, 11 or 12 fluorine atoms and further substituted by 0, 1, or 2 radicals selected from the group consisting of CH$_3$ and OCH$_3$;
R3, R4, R5, R6 and R7 are independently selected from the group consisting of hydrogen, F, Cl, Br, alkyl with 1, 2, 3 or 4 carbon atoms and substituted by 0, 1, 2, 3, 4, 5, 6, 7, 8 or 9 fluorine atoms, and alkoxy with 1, 2, 3 or 4 carbon atoms and substituted by 0, 1, 2, 3, 4, 5, 6, 7, 8 or 9 fluorine atoms, provided that R3 and R7 are not both simultaneously hydrogen.

3. The compound or salt of claim 2, wherein:
R1 and R2, together with the two carbon atoms to which they are bonded, form a five-, six- or seven-membered carbon ring comprising a double bond,
R3 and R7 are independently selected from the group consisting of F, Cl, Br and alkyl has 1, 2, 3 or 4 carbon atoms and is substituted by 0, 1, 2, 3, 4, 5, 6, 7, 8 or 9 fluorine atoms;
R4, R5 and R6 are H;
R8 is H or alkyl with 1, 2, 3 or 4 carbon atoms and substituted by 0, 1, 2, 3, 4, 5, 6, 7, 8 or 9 fluorine atoms.

4. The compound or salt of claim 3, which is selected from the group consisting of:
(2,6-dichlorophenyl)(4,5,6,7-tetrahydro-1H-benzoimidazol-2-yl)amine,
(2,6-dichlorophenyl)methyl(4,5,6,7-tetrahydro-1H-benzoimidazol-2-yl)amine, a pharmaceutically acceptable salt or trifluoroacetic acid salt of (2,6-dichlorophenyl)(4,5,6,7-tetrahydro-1H-benzoimidazol-2-yl)amine, and a pharmaceutically acceptable salt or trifluoroacetic acid salt of (2,6-dichlorophenyl)methyl(4,5,6,7-tetrahydro-1H-benzoimidazol-2-yl)amine.

5. The compound or a salt of claim 1, wherein R3, R4, R5, R6 and R7 are independently selected from the group consisting of hydrogen, F, Cl, Br, and alkyl with 1, 2, 3 or 4 carbon atoms and substituted by 0, 1, 2, 3, 4, 5, 6, 7, 8 or 9 fluorine atoms, provided that R3 and R7 are not both simultaneously hydrogen.

6. The compound or a salt of claim 5, wherein:
R3 and R7 are independently selected from the group consisting of F, Cl, Br and alkyl with 1, 2, 3 or 4 carbon atoms and substituted by 0, 1, 2, 3, 4, 5, 6, 7, 8 or 9 fluorine atoms;
R4, R5 and R6 are hydrogen;
R8 is either H or alkyl which has 1, 2, 3 or 4 carbon atoms and is substituted by 0, 1, 2, 3, 4, 5, 6, 7, 8 or 9 fluorine atoms.

7. A method of manufacturing a drug by incorporating a compound or a salt of claim 1, alone or in combination with one or more other drugs or active ingredients, in a pharmaceutically acceptable formulation for the treatment or prophylaxis of disorders of respiratory drive and/or of sleep-related respiratory disorders and sleep apneas.

8. The method of claim 7, wherein said drug is for the treatment or prophylaxis of snoring.

9. The method of claim 7, wherein said drug is for the treatment or prophylaxis of acute and chronic renal disorders, of acute renal failure or of chronic renal failure.

10. The method of claim 7, wherein said drug is for the treatment or prophylaxis of disorders of intestinal function.

11. A pharmaceutical composition for human, veterinary or phytoprotective use comprising an effective amount of one or more compounds or salts of claim 1.

* * * * *